United States Patent [19]
Doan

[11] Patent Number: 5,425,755
[45] Date of Patent: Jun. 20, 1995

[54] ROTATABLE PIN, SCREW-IN PACING AND SENSING LEAD HAVING TEFLON-COATED CONDUCTOR COIL

[75] Inventor: Phong D. Doan, Stevenson Ranch, Calif.

[73] Assignee: Pacesetter, Inc., Sylmar, Calif.

[21] Appl. No.: 235,203

[22] Filed: Apr. 29, 1994

Related U.S. Application Data

[63] Continuation of Ser. No. 985,383, Dec. 4, 1992, abandoned.

[51] Int. Cl.⁶ .............................................. A61N 1/36
[52] U.S. Cl. .................. 607/119; 128/642; 607/122
[58] Field of Search ............... 128/642; 607/119-132

[56] References Cited

U.S. PATENT DOCUMENTS

| | | | |
|---|---|---|---|
| 4,106,512 | 8/1978 | Bisping | 128/418 |
| 4,233,992 | 11/1980 | Bisping | 128/785 |
| 4,282,885 | 8/1981 | Bisping | 128/785 |
| 4,452,254 | 6/1984 | Goldberg et al. | 128/785 |
| 4,799,499 | 1/1989 | Bisping | 128/785 |
| 4,886,074 | 12/1989 | Bisping | 128/785 |
| 5,003,992 | 4/1991 | Holkman et al. | 128/786 |
| 5,020,545 | 6/1991 | Soukup | 128/786 |
| 5,076,285 | 12/1991 | Hess et al. | 128/786 |
| 5,152,277 | 10/1992 | Honda et al. | 128/4 |
| 5,174,295 | 12/1992 | Christian et al. | 128/662.06 |
| 5,183,464 | 2/1993 | Dubrul et al. | 128/3 |
| 5,318,525 | 6/1994 | West et al. | 607/122 |

*Primary Examiner*—William E. Kamm
*Assistant Examiner*—Marianne Parker
*Attorney, Agent, or Firm*—Malcolm J. Romano; Lisa P. Weinberg

[57] ABSTRACT

A rotatable pin, screw-in pacemaker lead assembly has a conductor coil enclosed within a silicone insulating tube. The conductor coil has a distal end secured to a helix electrode and a proximal end including a rotatable connector pin. The outer surface area of the conductor coil is coated with a super thin film of biocompatible Teflon. The Teflon coating substantially reduces the friction between the conductor coil and the inner wall of the insulating tube during lead fixation, thereby substantially reducing the number of turns of the connector pin required to effect fixation of the helix electrode.

4 Claims, 3 Drawing Sheets

ROTATABLE PIN, SCREW-IN PACING AND SENSING LEAD HAVING TEFLON-COATED CONDUCTOR COIL

This is a continuation of application Ser. No. 07/985,383, filed on Dec. 4, 1992, now abandoned.

FIELD OF THE INVENTION

The present invention relates generally to implantable medical devices for providing stimulating pulses to selected body tissue, and more particularly, to the lead assemblies connecting such devices with the tissue to be stimulated.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers for providing precisely controlled stimulation pulses to the heart. However, the appended claims are not intended to be limited to any specific example or embodiment described herein.

Pacemaker leads form the electrical connection between the cardiac pacemaker pulse generator and the heart tissue which is to be stimulated. As is well known, the leads connecting such pacemakers with the heart may be used for pacing, or for sensing electrical signals produced by the heart, or for both pacing and sensing in which case a single lead serves as a bidirectional pulse transmission link between the pacemaker and the heart. An endocardial type lead, that is, a lead which is inserted into a vein and guided therethrough into a cavity of the heart, includes at its distal end an electrode designed to contact the endocardium, the tissue lining the inside of the heart. The lead further includes a proximal end having a connector pin adapted to be received by a mating socket in the pacemaker. A flexible, coiled conductor surrounded by an insulating tube or sheath couples the connector pin at the proximal end and the electrode at the distal end.

To prevent displacement or dislodgement of the electrode and to maintain the necessary stable electrical contact between the lead tip and the endocardial tissue, the electrode must be firmly anchored relative to the tissue. To achieve this, the electrode of one known type of lead comprises a pointed helix adapted to be screwed into the heart tissue to be stimulated. Rotational torque applied to the connector pin at the proximal end of the lead is transmitted via the flexible, coiled conductor to the helical electrode which is thereby screwed into the heart tissue. In this fashion, the position of the electrode tip is mechanically stabilized, that is, the tip is positively anchored so as to remain securely in place during the lifetime of the implant. Removal of the screw-in electrode from the endocardium can be effected by counter rotation of the connector pin. Thus, in a rotatable pin, screw-in lead the conductor coil is used not only as an electrical conductor coupling for the connector pin and the helix electrode, but also as a tool for extending or retracting the helix electrode relative to the distal tip of the lead during lead myocardium fixation by rotating the connector pin.

It is desirable to minimize the number of revolutions of the lead connector pin required to fully extend or retract the helix electrode during lead fixation. The number of connector pin turns is a function of several factors:

(a) conductor coil stiffness, with a stiffer coil requiring fewer connector pin turns (a very stiff conductor coil, however, results in a very stiff lead that potentially creates problems such as high chronic pacing threshold or tip myocardium perforation);

(b) friction between the helix electrode and seal, where such a seal is utilized to prevent ingress of bodily fluids;

(c) the length of the lead body (a longer lead requires more turns of the connector pin to advance or retract the helix electrode a given distance); and (d) friction between the conductor coil and the surrounding insulating sheath or tube.

With respect to factor (d), to minimize frictional resistance between the "torque transfer" conductor coil and the surrounding insulation tubing, polyurethane tubing has been preferred over silicone tubing because the coefficient of friction between conductor coils (such as the multifilar MP35N conductor coil utilized in various screw-in pacemaker leads manufactured by Siemens Pacesetter, Sylmar, Calif., U.S.A.) and polyurethane tubing is less than that between such coils and silicone tubing. However, because the use of polyurethane tubing has several disadvantages, such as stiffness and limited long term biostability, it would be desirable to use silicone tubing instead.

Accordingly, it is an overall object of the present invention to provide a screw-in lead assembly using silicone insulation tubing but in which the friction between the conductor coil and tubing, and hence the torque and number of connector pin turns required to extend or retract the helix electrode, is substantially reduced.

SUMMARY OF THE INVENTION

In accordance with the broader aspects of the present invention, the foregoing object is attained in a screw-in lead assembly employing silicone insulation tubing by coating the outer surface area of the conductor coil with a super thin biocompatible Teflon (polytetrafluoroethylene). It has been found that such a coating significantly reduces the torque required to extend or retract the helix electrode thereby making the use of silicone insulation tubing in screw-in leads substantially more advantageous than polyurethane tubing. Indeed, comparison tests between uncoated and Teflon-coated conductor coils within silicone tubing have demonstrated that the coated conductor coil decreases the torque required to rotate the coil by approximately 67%.

BRIEF DESCRIPTION OF THE DRAWINGS

Further objects, features and advantages of the invention will become apparent from the Detailed Description of the Preferred Embodiments when read in conjunction with the accompanying drawings, in which.

DETAILED DESCRIPTION OF THE PREFERRED EMBODIMENTS

The following description presents several preferred embodiments representing the best mode contemplated for practicing the invention. This description is not to be taken in a limiting sense but is made merely for the purpose of describing the general principles of the invention whose scope is defined by the appended claims.

Figure 1:
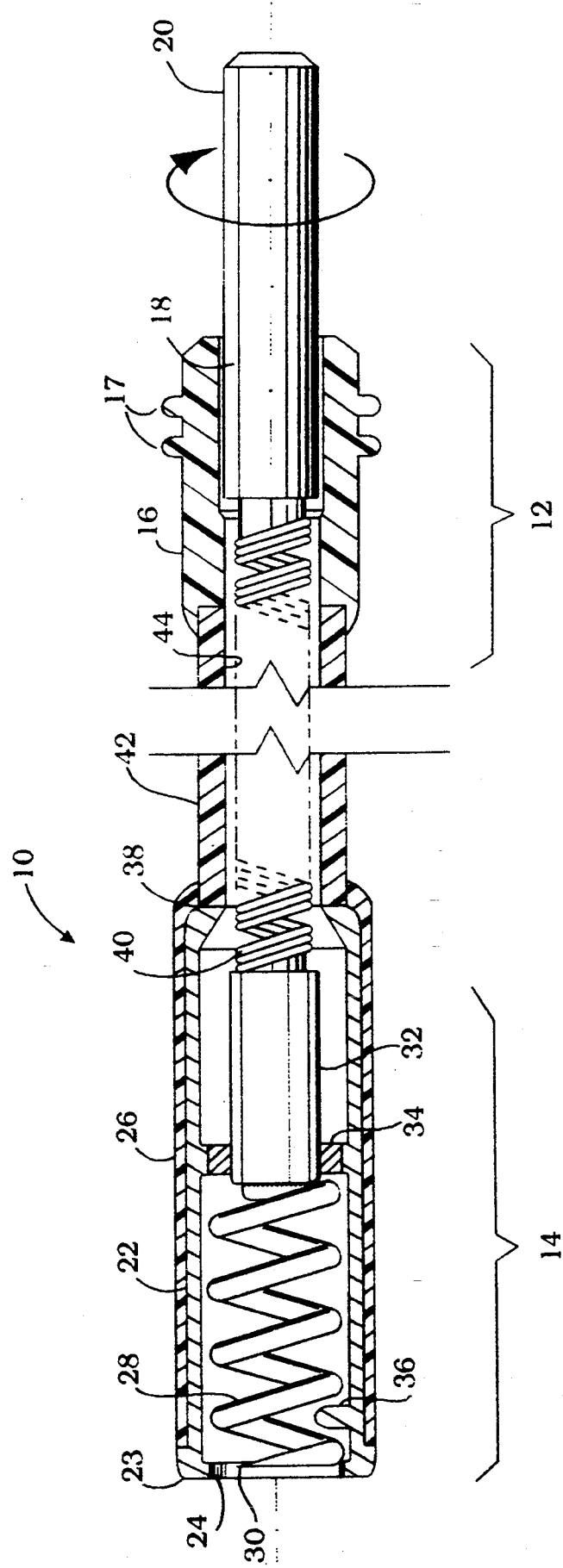
FIG. 1 is a somewhat schematic, longitudinal cross section of a screw-in lead assembly having a conductor coil whose outer surface area has been coated in accordance with the invention.

Referring to FIG. 1, there is shown a unipolar screw-in pacing lead 10 having a proximal end 12 and a distal end 14. The proximal end 12 is adapted to be plugged into a receptacle in a cardiac pacemaker (not shown) and includes a tubular housing 16 made of an insulating biocompatible material such as silicone. The tubular housing 16 includes annular ribs 17 for sealing the pacemaker receptacle against the entry of bodily fluids. The tubular housing 16 encloses a generally cylindrical, rotatable connector pin 18 having a portion 20 projecting from the proximal end of the housing 16. The pin portion 20 is adapted to be received by a pacemaker socket coupled to the pulse generating and pulse sensing circuits within the pacemaker.

The distal end 14 of the lead 10 includes a metallic, tubular housing 22 including a distal tip 23 having an opening 24. Except for the ring-shaped tip 23 the tubular housing 22 is enclosed within an insulating sheath 26. The distal end 14 of the lead 10 further includes a rotatable, extendable/retractable helix electrode 28 shown in FIG. 1 fully retracted within the tubular housing 22. As is well known, the helix electrode 28 serves both as a fixation means to securely anchor the distal end of the lead relative to the tissue to be stimulated and as an electrically conductive contact element for transmitting electrical stimulation and sensed pulses. The helix electrode 28, which may be made of a platinum-iridium alloy, for example, has a sharp end 30 adapted to pierce the endocardial tissue.

The helix electrode 28 is carried by a shaft 32 welded or otherwise secured to the proximal end of the electrode 28. The shaft 32, in turn, is carried by a fluid-tight seal 34 mounted within the tubular housing 22, the shaft being rotatably and axially movable relative to the seal 34. Projecting inwardly from the inner wall of the tubular member 22 proximate the tip 23 is a post 36 interposed between adjacent turns of the helix electrode 28. In this fashion, rotation in one direction or the other of the helix electrode 28 within the tubular housing 22 will cause the helix electrode to be extended or retracted relative to the tip 23.

The shaft 32 and connector pin 18 are electrically and mechanically coupled by means of a conductor coil 38 having an outer surface area 40 along the length of the conductor coil. The conductor coil 38 is housed within an insulating tube 42 interconnecting the tubular housings 16 and 22 and having an inner wall 44. In accordance with an aspect of the invention, the tube 42 is made of silicone.

It will thus be seen that given the helical sense of the electrode 28 illustrated in FIG. 1, rotation of the connector pin 18 in a clockwise direction (as viewed from the proximal end of the lead) will cause advancement of the helix electrode and its extension from the opening 24 in the tip 23 of the tubular housing 22 to a fully extended position, while rotation of the connector pin in a counterclockwise direction will result in retraction of the electrode 28 to its fully retracted position shown in FIG. 1. As already explained, the number of turns of the connector pin required to fully extend or fully retract the helix electrode is a function of several factors among which is the friction between the outer surface area 40 of the conductor coil 38 and the inner wall 44 of the insulation tube 42. It has been found that such friction, and therefore the number of turns required for full extension or retraction of the helix electrode, can be substantially reduced by coating the outer surface area 40 of the conductor coil with a super thin film of biocompatible Teflon. Accordingly, once the situs of lead fixation has been determined, fixation is effected both expeditiously and without displacement of the tip relative to the fixation location which might otherwise occur if friction levels were higher.

The retracting spring force imposed by the conductor coil 38 on the helix electrode maintains the helix electrode 28 in electrical contact with the metallic tubular housing 22 via the conductive post 36. In this fashion, the ring tip 23 permits threshold mapping of the heart tissue prior to lead fixation.

Figure 2:
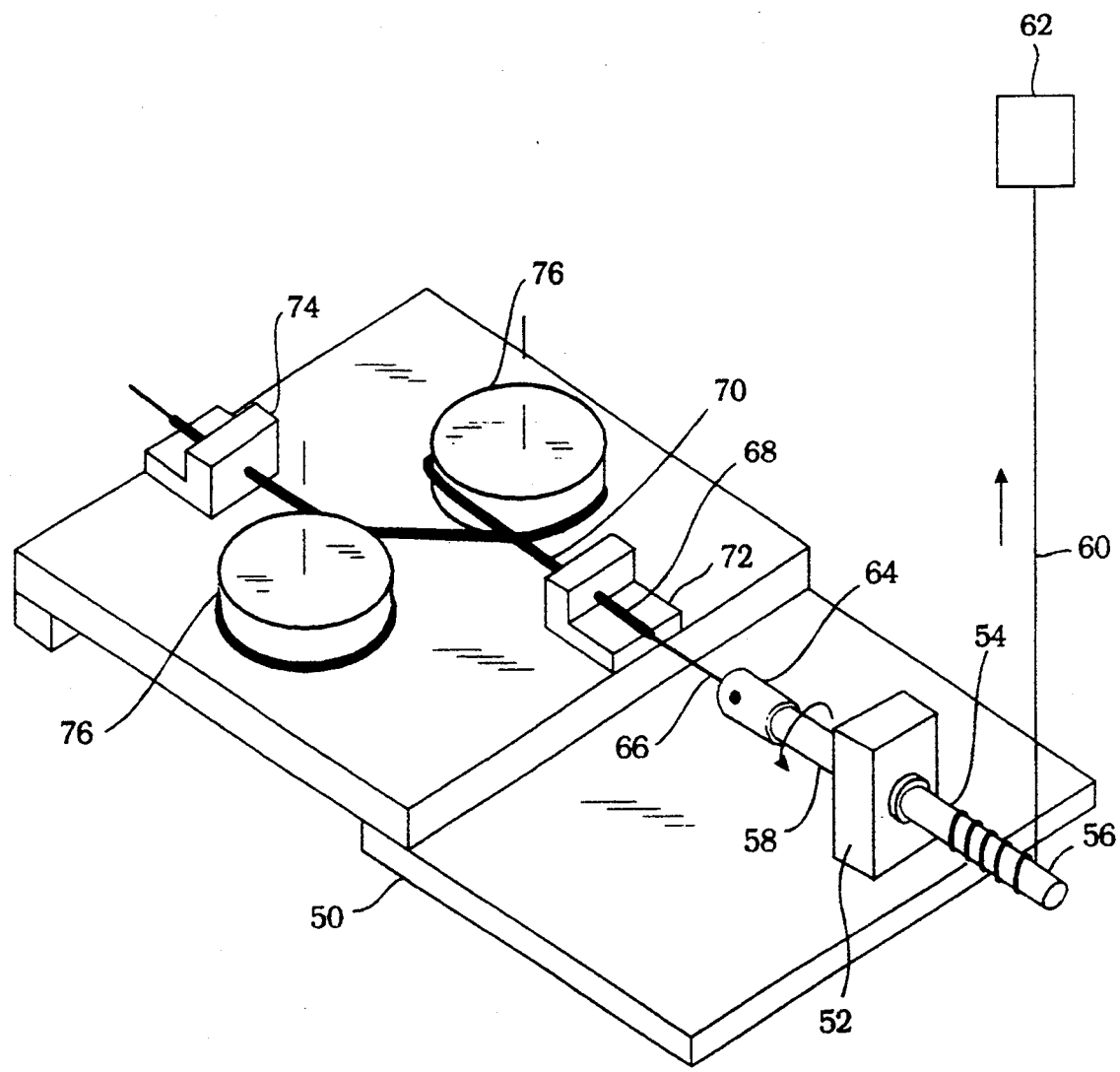
FIG. 2 is a perspective view of a test fixture for performing torque tests on screw-in type lead assemblies.

FIG. 2 shows a fixture for performing comparative torque tests on rotatable pin, screw-in type lead assemblies. The fixture includes a base 50 having mounted adjacent one end thereof a low friction bearing block 52. A shaft 54, rotatably carried by the bearing block 52, has an outer end portion 56 and an inner end portion 58. Wrapped around the outer end portion 56 of the shaft is a thread 60 having a vertical run coupled to a device 62 for pulling the thread upwardly at a predetermined velocity and for measuring the force required to rotate the shaft 54.

The inner end portion 58 of the shaft 54 carries a clamp 64 to which is secured one end of a conductor coil 66 of a selected length of test lead 68. The test lead 68, which includes outer insulative tubing 70, is held in place by anchoring blocks 72 and 74 mounted on the base 50. The free end of the lead 68 projects from the block 74. The portion of the lead 68 between the blocks 72 and 74 is wound around a pair of space apart cylinders 76 mounted on the base 50 so as to introduce resistance to the rotation of the conductor coil 66 within the insulative tubing 70. By way of example, each cylinder may have a diameter of 2.0 inches and the spacing between the axes of the cylinders is 3 inches. It will thus be seen that for a given diameter of the shaft 54, the force required to pull the thread is a measure of the torque required to rotate the conductor coil 66 within the insulative tubing 70. (It will be understood that the friction force introduced by the bearing block 52 can be separately measured and subtracted out.)

Figure 3:
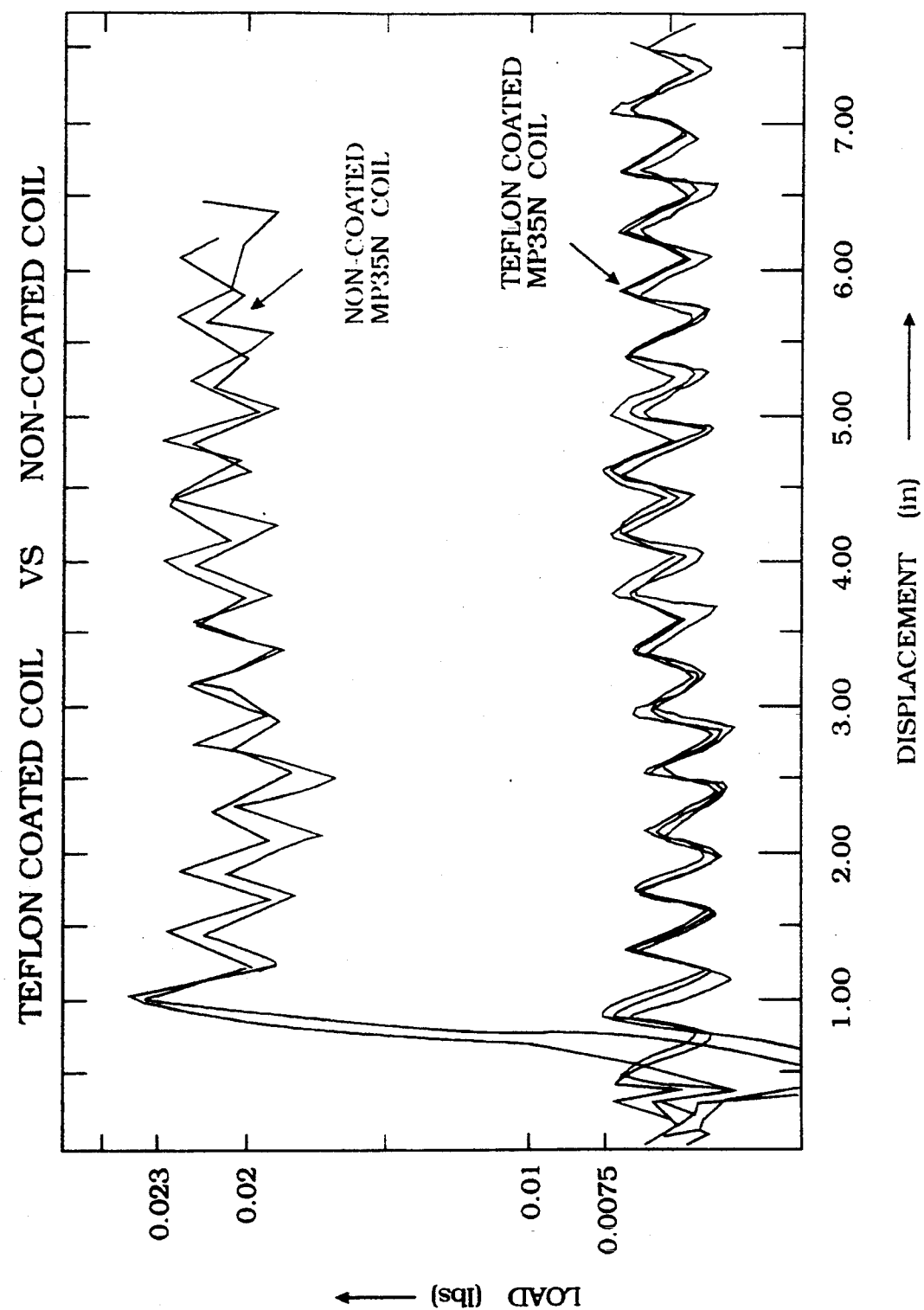
FIG. 3 is a graph comparing the forces required to rotate uncoated and Teflon-coated conductor coils of lead assemblies using silicone insulation tubing.

FIG. 3 is a graph of load (lbs) v. displacement (inches) showing typical results of torque tests using the test fixture of FIG. 2 performed on (1) a test lead comprising silicone insulative tubing with a Teflon-coated conductor coil and (2) a test lead (of the same length as the first test lead) comprising silicone insulative tubing with an uncoated conductor coil. Each test lead had a length of 21 inches and the thread was advanced at a rate of 40 inches per minute. The diameter of shaft 54 was 0.125 inch. In the examples reported in FIG. 3, two test runs were performed on the lead incorporating the noncoated coil while three test runs were performed on the test lead having the Teflon-coated coil. In both cases, the conductor coil 66 was a standard MP35N multifilar coil.

It will be seen that the results of the comparative tests illustrated in FIG. 3 show a dramatic reduction in the force required to rotate the conductor coil 66 when coated with Teflon. The average peak force required to rotate the noncoated coil is approximately 0.023 lb. while the average peak force required to rotate the coated coil is 0.0075 lb., a reduction of about 67%.

Although the present invention has been described in terms of unipolar pacing lead assemblies it will be understood that the invention is applicable as well to bipolar pacing leads having two separate conductors, and to multipolar pacing leads employing multiple conductor leads.

What is claimed is:

1. An implantable active-fixation cardiac pacing lead adapted to transmit electrical pulses between a proximal end of the lead and a distal end of the lead and to stimulate cardiac tissue, said distal end having a distal tip, the lead including:
    a silicone rubber insulating tube extending between the proximal and the distal ends of the lead, the insulating tube having an inner wall;
    a conductor coil, located within the insulating tube, for transmitting the pulses, the conductor coil having a proximal end coupled to the proximal end of the lead, a distal end coupled to the distal tip of the lead, and an outer surface area, the outer surface area of the conductor coil having a biocompatible, lubricious coating for reducing friction between the conductor coil and the inner wall of the insulating tube; and
    a helix electrode connected to the distal end of the conductor coil for engaging the tissue to be stimulated, the conductor coil being adapted to extend or retract the helix electrode relative to the distal tip of the lead through rotation of the proximal end of the conductor coil;
    whereby a torque force applied at the proximal end of the conductor coil is translated to the distal end with minimal friction so that the number of rotations required to extend or retract the helix electrode is substantially reduced.

2. The implantable lead, as defined in claim 1, wherein:
    the conductor coil includes at the proximal end thereof a connector pin, torque manually applied to the connector pin effecting said extension or retraction of the helix electrode.

3. The implantable lead, as defined in claim 1, wherein:
    the coating comprises a thin film of biocompatible Teflon.

4. An implantable active-fixation cardiac pacing lead having a proximal end and a distal end, comprising:
    a proximal connector assembly located at the proximal end of the lead, the proximal connector assembly having a connector pin rotatable within a tubular, insulative housing;
    a distal electrode assembly located at the distal end of the lead, the distal electrode assembly having an extendable and retractable helix electrode for actively engaging cardiac tissue;
    a silicone rubber insulating tube extending between the proximal connector assembly and the distal electrode assembly, the insulating tube having an inner wall; and
    a conductor coil connected at one end to the connector pin and at the other end to the helix electrode, the conductor coil having an outer surface coated with a thin film of biocompatible Teflon coating, the conductor coil transferring a manually applied torque force from the connector pin to the helix electrode through rotation of the conductor pin, whereby the Teflon coating reduces friction between the conductor coil and the insulating tube thereby reducing the torque force needed to engage the helix into adjacent cardiac tissue.

* * * * *